United States Patent [19]

Byers et al.

[11] Patent Number: 5,643,572

[45] Date of Patent: Jul. 1, 1997

[54] METHODS AND COMPOSITIONS FOR THE MODULATION OF HOST IMMUNE RESPONSE TO AN ALLERGEN

[75] Inventors: Vera K. Byers, San Francisco, Calif.; Robert W. Baldwin, Long Eaton, England

[73] Assignee: Allergene, Inc., San Mateo, Calif.

[21] Appl. No.: 157,843

[22] Filed: Nov. 24, 1993

Related U.S. Application Data

[63] Continuation of Ser. No. 549,184, Jul. 6, 1990, abandoned.

[51] Int. Cl.$^6$ .................... C07K 16/00; A61K 39/395
[52] U.S. Cl. .................... 424/171.1; 424/130.1; 530/387.1; 530/388.1; 530/388.15; 530/863; 530/862; 530/868
[58] Field of Search .................... 424/130.1, 71.1; 530/387.1, 388.1, 388.15, 863, 862, 868

[56] References Cited

PUBLICATIONS

Morikawa et al., 1990, "B–Cell mediated regulation of delayed–type hypersensitivity," Cellular Immunology 131:338–351.

Baskar et al., 1990, "The presentation of L–tyrosine–a–zobenzenearsonate by different mouse Ia molecules uses a common agretope," Mol Immunol 27:79–86.

Romani et al., 1989, "Cultured human Langerhans cells resemble lymphoid dendritic cells in phenotype and function," J Invest Dermatol 93:600–609.

Rajnavolgyi et al., 1989, "Structural characteristics influencing the carrier function of synthetic branched polypeptides based on poly[Lys–(DL–Ala)3] backbone," Mol Immunol 26:949–958.

Bigby et al., 1989, "Production of hapten–specific T cell hybridomas and their use to study the effect of ultraviolet B irradiation on the development of contact hypersensitivity," J Immunol 143:3867–3872.

Owhashi et al., 1988, "Protection from experimental allergic encephalomyelitis conferred by a monoclonal antibody directed against a shared idiotype on rat T cell receptors specific for myelin basic protein," J Exp Med 168:2153–2164.

Kappler et al., 1988, "Self–tolerance eliminates T cells specific for Mls–modified products of the major histocompatibility complex," Nature 332:35–40.

Thomas et al., 1987, "Production of monoclonal antibodies selective for aggregation–competent chick neural retina cells. An immunosuppressive approach," J Immunol Methods (Netherlands) 97:237–243.

Eddy et al., 1987, "Idiotype regulation of the anti–bovine serum albumin response," J Immunol 138:1693–1698.

Buus et al., 1987, "The interaction between protein–derived immunogenic peptides and Ia," Immunol Rev (Denmark) 98:115–141.

Morrison et al., 1984, "Chimeric human antibody molecules: mouse antigen–binding domains with human constant region domains," Proc Nat Acad Sci USA 81:6851–6855.

Infante et al., 1982, "Definition of T cell idiotypes using anti–idiotypes using anti–idiotypic antisera produced by immunization with T cell clones," J Exp Med 155:1100–1107.

Epstein et al., 1982, "Induction of antigen specific hyposensitization to poison oak in sensitized adults," Arch Dermatol 118:630–633.

Dunn et al., 1982, "A murine model system for contact sensitization to poison oak or ivy urushiol components," Cellular Immunol 68:377–388.

Epstein et al., 1981, "Induction of persistent tolerance to urushiol in humans," J Allergy Clin Immunol 68:20–25.

Claman et al., 1980, "Suppressive mechanisms involving sensitization and tolerance in contact allergy," Immunol rev (Denmark) 50:105–132.

Stockinger et al., 1979, "On the feedback regulation of humoral immune response I. Evidence for 'B suppressor cells'," Immunology 36:87–94.

McConnell, 1971, "Studies on actively allergized cells. III. Suppression of the allergic response with specific antibody and the effect of this treatment on plaque— and rosette–forming cells," International Archives if Allergy 40:287–304.

Baer et al., 1970, "The immunochemistry if immune tolerance. II. The relationship of chemical structure to the induction of immune tolerance to catechols," J Immunol 104:178–184.

Baer et al., 1967,"Delayed contact hypersensitivity to catechols. II. Cutaneous toxicity of catechols chemically related to the active principles of poison ivy," J Immunol 99:365–369.

(List continued on next page.)

Primary Examiner—Frank C. Eisenschenk
Attorney, Agent, or Firm—Pennie & Edmonds LLP

[57] ABSTRACT

The present invention provides novel compositions and methods useful in the, modulation or selective suppression of host immune responses to an immunogen of interest, particularly exogenous antigens and allergens such as urushiol, the active plant component causing poison ivy/oak contact sensitivity. The subject compositions are antibody molecules of either $Ab_1$ or $Ab_2$(anti-idiotypic) reactivity with respect to the sensitizing antigen. Other compositions include specific T cell receptor (TCR) molecules either as T cell clones or hybridomas or as TCR preparations. Immunogenic peptides corresponding to some or all of the complementary determining regions or hyper-variable regions of the TCR are also employed. Such compositions suppress host immune responses to antigen by a variety of pathways including anti-idiotypic interactions with cells involved in antigen processing and stimulation of the immune network. T cell receptor molecules and immunogenic peptides corresponding to regions of the TCR also suppress immune responses by interactions with the immunoregulatory network.

8 Claims, No Drawings

PUBLICATIONS

Devich et al. Clinical Nephrology 3(3):106–113 (1975).
Harris et al Tibtech 11:47–44 (1993).
Osband et al. Immunotherapy 11(6):193–195 (1990).
Dillmon Ann. Int. Mel. 111:592–600 (1989).
Bird et al Grenis & Cancer Chapter 17 (1990).
Mascola et al. JAMA 272(6):488–489 (1994).
Bioworld Today 4(101) 1&4 1993 Allergene Is Itching To Fight Poison Oak.
Jonak et al Adv. Drug Delive Rev 2:207–228 1988.
Abramoinicz et al New Eng J. Med. Sep. 3, 1992 p. 736.
Sikorska J. Biol. Resp. Med 7:327–358 1988.
Kalish et al J. Clin. Invest 82:825–832 1988.
Riechmann et al. Nature 332:323–327 1988.
Ostberg et al. Hybridoma 2:361–367 1983.
Dunn et al. J. Investigative Dermatology 89:296–298 1987.
Waldmann Science 252:1657 1991.
Paul Fundamental Immunology 1984 p. 229.
Liberato, et al J. Med. Chem. 24:28–33 1981.
Kurata, et al. J. Immunology 144:4526–4535 1990.

METHODS AND COMPOSITIONS FOR THE MODULATION OF HOST IMMUNE RESPONSE TO AN ALLERGEN

This is a continuation, of application Ser. No. 07/549,184, filed Jul.6, 1990, now abandoned.

BACKGROUND OF THE INVENTION

Field of the Invention

This invention relates generally to the field of immunology and, more particularly, to methods and compositions for the modulation of host immune response to an immunogen, particularly exogenous antigens such as allergens, employing antibody or T cell receptor compositions.

Mammalian host immune response may be provoked by a variety of stimuli, including pathogens and allergens, and all involve T lymphocytes, either indirectly as helper cells which stimulate B cells to produce antibodies against these agents, or directly as T cells producing the direct response.

Poison oak and ivy dermatitis is but one example of a direct T cell mediated allergic reaction. This reaction occurs against the antigen urushiol which contacts the skin, bronchial epithelium, or the like. It s a leading cause of worker's compensation in the United States, and affects more than 80% of Americans. The antigen is an oil, and is essentially the same in poison oak, ivy, and sumac. The oil is found in the leaves and sap of the plant and is quite stable. Dermatitis can result from direct contact with the plant itself or from contact with fomites, such as the coat of a dog, or shoes worn through a patch of the plant. The allergic reaction is usually manifest as a dermatitis, but can also appear as a severe bronchitis produced by inhaling smoke from a fire containing poison oak, since the oil can coat microscopic particles in the soot and be inhaled. In some cases the reaction can be life threatening, such as with recurrent episodes which damage the skin barrier and allow systemic infections to occur. In most cases, however, it primarily affects one's ability to work (especially individuals who cannot avoid exposure as part of their work, e.g. farm workers, fire fighters, or the like) and quality of life.

As with most allergens, individuals vary in the extent of their sensitivity to urushiol. Skin testing can predict those individuals who will be most affected by the reaction. The effective amount of urushiol in one leaf is about 2 µg. Those individuals developing reactions to direct application of less than 0.05 pg are termed "exquisitely sensitive". It can be predicted that they will develop dermatitis upon even minimal exposure. Those individuals requiring about 0.05–2.5 µg for reaction are termed "moderately sensitive". Such individuals can tolerate modest exposure to urushiol.

It has been known for many years that oral administration of urushiol in gradually increasing doses over a period of 3–6 months can produce hyposensitization. Epstein, W., et l.,*Arch. Dermatol.* (1982)118:630–633. This means that the individual requires larger doses of urushiol to develop the dermatitis following hyposensitization treatment. Thus, an "exquisitely sensitive" individual can be converted to a "moderately sensitive" individual with the accompanying clinical advantages. It is necessary to monitor these patients closely, since too rapid acceleration of the doses can result in pruritus or other manifestations of allergic reaction. Although the procedure is thus rather unwieldy due to potential allergic reaction, hyposensitization in this manner can last up to one year or more. In addition, it has been shown that a single series of three weekly intramuscular injections in nonsensitized individuals can protect them from sensitization to urushiol for up to 7 years. Epstein, W., et al., *J. Allergy Clin. Immunol.* (1981)68:20–25. This approach is not feasible for adults since most of those who are susceptible to sensitization have already become so and intramuscular injection of urushiol in such a sensitized individual is associated with significant morbidity. Nevertheless, it does indicate that administration of antigen is capable both of blocking sensitization (tolerance) or decreasing reactivity (hyposensitization).

The active ingredient in poison oak/ivy, urushiol, is a mixture of four closely related alkylcatechols. All have the same catechol ring, and an alkyl side chain of 15 or 17 carbons, with various degrees of unsaturation ranging from zero to three double bonds. The catechol ring is capable of spontaneously forming covalent bonds with larger molecules which mount a nucleophilic attack upon the catechol ring. This is presumed to be a necessary step in activation since closely related molecules with ring structures incapable of such bond formation are not immunogenic. Urushiol is intensely hydrophobic, dissolves rapidly into the skin, and presumably penetrates rapidly into the epidermis to the Langerhans cells.

The animal models that have been most utilized for investigation of the mechanism of action of urushiol hypersensitivity dermatitis have been the guinea pig and the mouse. The guinea pig develops a direct dermatitis after sensitization and challenge. This dermatitis closely resembles the dermatitis noted in humans including erythema, induration, and blistering at higher doses. The mouse s usually sensitized by abdominal painting and challenged on the ear; reactivity is manifest as ear swelling. The guinea pig has been primarily utilized for experiments with urushiol analogues, and it was in this species that the importance of the catechol ring was demonstrated. Baer, H., et al., *J. Immunol.* (1970)104:178–184. The mouse, because of its inbred availability has been utilized for cell and serum transfer experiments. It was demonstrated in the mouse that urushiol reactivity could be transferred through T lymphocytes. Dunn, L, et al., *Cell. Immunol.* (1982):68:377–388. Following sensitization, there is a period of time (about 1 month) where challenge with urushiol or its components can still elicit a response. After this time, however, the mouse becomes refractory to challenge. Suspecting that this refractory phase represented active tolerance, it was demonstrated that T lymphocytes taken from animals during this period could transfer resistance to sensitization (tolerance) to virgin animals. Further, it was shown that serum from animals during this time were also capable of suppressing reactivity, suggesting that serum factors were present in the donor animals which either directly blocked sensitization, or produced suppressor cells which blocked sensitization, or both. Dunn, I., et al., *J. Invest. Dermatol.* (1987)89:296–298.

Because of its low molecular weight (320) Da urushiol falls into the class of compounds termed haptens. These chemicals can be potent immunogens (sensitizers) and are capable of inducing both T cell mediated immunity, and B cell mediated immunity (antibodies). Before they can exert this action, however, they must first be coupled to higher molecular weight molecules. Such molecules can range from serum proteins such as human serum albumin (HSA) to self cell bound molecules such as those of the major histocompatibility loci (MHC molecules). In most cases the bond must be covalent although some haptens such as nickel may be able to produce this effect by very firm non-covalent binding. Urushiol and its components are presumed to form this covalent bond spontaneously in vivo by oxidation of the catechol ring to a quinone and resultant hydrophilic attack by a larger molecule which can serve as the carrier. Since these carrier molecules can form part of the eventual antigen that is recognized by either T cells or antibody, it is often difficult to predict what the actual specificity of the immune response will be. In the case of animal models of some autoimmune diseases, such as experimental autoimmune encephalomyelitis used as a model for multiple sclerosis, the antigen causing the disease has been identified as myelin basic protein, and it is recognized in conjunction with the individual MHC molecules of each animal. Acha-Orbea, H., et al., *Ann. Rev. Immunol.* (1989)7:371–405. Thus the specificity of the T cell receptor (TCR) or of antibodies recognizing the complex will be different between animals with different MHC molecules. This is the case with most other animal models of autoimmune diseases. In contrast, a common MHC association site has been identified for some haptens, so it is possible that the specificity of the TCR or antibodies may be common between different animals. Baskar, S., et al., *Mol. Immunol.* 1990)27:79–86.

A wide variety of experimental haptens are known to produce delayed type hypersensitivity reactions (DTH). As in the case of urushiol, the tolerance can be transferred by T cells which are termed suppressor cells). Other work has demonstrated that anti-idiotypic antibodies can also transfer tolerance. Claman, H., et al., *Immunol. Rev.* (1980) 50:105–132. It has therefore been suggested that at least one mechanism of tolerance in these cases is the generation of either anti-idiotypic antibodies, suppressor cells, or both, all of which can induce tolerance. In an animal system this tolerant state may be the usual sequelae of an immune response after antigen challenge, but appropriate manipulation of the system could allow the induction of this state without the initial dermatitis.

Antibodies reacting with a specific antigen can themselves suppress antibody responses to that antigen. This has been demonstrated with particulate antigens such as sheep erythrocytes, and proteins where administration of antibody both before or following antigen stimulation suppressed antibody responses in the recipient. Krieger-Eddy, N., et al., *J. Immunol.* (1987)138:1693–1698. The specificity of antibody induced immune suppression is quite variable since in some cases antibodies reacting with one epitope will suppress antibody responses to the whole antigen. In other cases antibody treatment only suppresses responses to the epitope recognized by the treating antibody. This approach for controlling immune responses to haptens is particularly attractive, since molecules such as urushiol only have a few (often no more than one) epitopes. (An epitope is the simplest form of an antigenic determinant present on a complex antigenic molecule.)

The mechanism of action of antibody mediated suppression of immune responses is not clear. Removal of antigen from the system is possible although more specific mechanisms have been proposed to account for studies where antibody treatment was effective when given after antigen stimulation. These include antibody inhibition of antigen processing at the level of interaction of antigen processing cells and interactions with T helper cells possibly by antibody binding to the T cell receptor (TCR), as well as inhibition of antigen specific B cells.

The immune system is now considered to be composed of network (idiotypic network) in which components can stimulate or down regulate immune responses. See e.g. Wigzell & Bing, *Progress in Immunology IV,* eds. Fougereau & Dausset (Academic Press, N.Y.) p. 94–103 (1980); Infante, et al., *J. Exp.* (1982)155:1100; Bona & Paul, *Regulatory T Lymphocytes,* eds. Pernis & Vogel (Academic Press, N.Y.) p. 292 (1980); WO 84/02848. The antigen is considered to induce an antibody ($Ab_1$) or an immune T lymphocyte having a TCR. These in turn can stimulate anti-idiotypic antibodies ($Ab_2$). These anti-idiotypic antibody responses generate families of antibodies recognizing the combining site of the first antibody ($Ab_1$) and/or related structures. These anti-idiotypic antibodies provide a means for altering T cell and B cell responses, one component being down regulation of immune responses to the original antigen. Anti-idiotypic antibodies can also stimulate antibody responses to produce anti-anti-idiotypic antibodies ($Ab_3$) which in some cases react with the original antigen.

Although anti-idiotypic antibodies have been shown multiple systems to down regulate the immune response, recent data indicates more potent reagents for this may be either the T cell receptor itself, (with specificity similar to $Ab_1$) used as active vaccination, or anti-idiotypic antibodies against the TCR (equivalent to $Ab_2$, used for passive therapy). The reason for this relates to the specificity of the antibody. Since antigens are recognized in association with class II MHC antigens, the actual TCR has a specificity recognizing the antigen in association with the class II MHC. In other systems this specificity is so exquisite that the specificity of a TCR against a given antigen will differ between individuals and species of inbred animals, since the portion of the MHC co-recognized is variable between individuals. However it has recently been shown that many antigens are recognized in conjunction with a region of the MHC which is common to many species (called an agretope). This has suggested that a superior immunogen may be constructed by using antigen coupled to this common portion of the MHC, which would be an effective vaccine in all individuals, and indeed in animal systems as well. In addition, an antibody made against the anti-urushiol TCR isolated from one individual should serve as an effective agent for passive immunotherapy in other individuals as well.

This hypothesis has been recently tested by demonstrating that the immunoglobulin fraction of patients hyposensitized (by oral administration) to urushiol contained a fraction which could abrogate the sensitization of mice to urushiol. This suggests that the effect was produced either by $Ab_1$ or $Ab_2$, which can cross species (Stampf, J.L. et. al.J. Invest. Derm. 95:363–365, 1990). If the $Ab_2$ is directed against the TCR, as the literature would suggest is the case, this finding indicates that the reactivity of such antibodies is not even limited to the same species.

There is compelling evidence that T cells recognize antigen in the context of MHC molecule, this occurs on the surface of antigen presenting cells. A strong correlation between MHC restrict-on of response to a particular antigenic determinant and its ability to bind to purified MHC molecules has been demonstrated. Buus, S., et al., *Immunol. Rev.* (1987)98:115–141. The small synthetic hapten L-tyrosine p-azobenzenearsonate (ABA-tyr) is immunogenic n several mouse haplotypes and it has been shown that the azo linked benzene groups of the hapten function as an agretope. Based upon a hypothetical model of the MHC class II protein (Brown, J. H., et al., Nature (1988)329:845) the hydrophobic residues ($Tyr^{30}$, $Ile^{31}$, $Tyr^{32}$, $Tyr^{37}$, and $Val^{38}$) in the $B_1$ domain form a hydrophobic patch on the binding cleft and have been suggested as likely contact points for the agretope of ABA-tyr. Goodman, J. W., *Chem. Immunol.* (1989)46:1. This hydrophobic region is a conserved characteristic of all Ia molecules.

The allergenic properties of alkylcatechols such as urushiol are dependent upon their reactivity towards nucleophiles such as amino or thiol groups of amino acids. Baer, et al., *J. Immunol* (1967)99:365. In addition, allergic potency is dependent upon the side chain and the presence of unsaturated bonds. From these findings it has been predicted that the hydrophobic allergen urushiol interacts with a common internal agretope on MHC molecules by covalent bond formation through the quinone ring and hydrophobic structures between the alkyl side chain and MHC with MHC restriction being minimal. This has led to several approaches for inducing immune responses to these haptens. These include formation of urushiol conjugates with MHC protein preparations as well as peptides containing sequences like the predicted internal agretope. Other approaches involve treating antigen processing cells such as cultured human Langerhans cells (Romani, N., et al., *J. Invest. Derm.* (1989)93:600-09) or mouse peritoneal macrophages with urushiol.

The present invention relates to the down regulation of immune response to exogenous antigens such as the allergen urushiol by manipulating the idiotypic network. This can be effected by the use of TCR's, $Ab_1$, or $Ab_2$, all with specificity directed against the antigen either alone or in combination with other carriers. The advantage of this more direct approach over older methods is that side effects related to prolonged antigen administration are avoided, the procedure is faster and more effective, and the use of limited epitopes make the procedure feasible in cases where antigen hyposensitization is not possible. Urushiol is used as an example of the procedures, which should be applicable to any exogenous antigen or allergen in which dominant epitope(s) can be identified.

SUMMARY OF THE INVENTION

The present invention provides novel compositions and methods useful in the modulation or selective suppression of host immune responses to an immunogen of interest, particularly exogenous antigens and allergens such as urushiol, the active plant component causing poison ivy/oak contact sensitivity. The subject compositions are antibody molecules of either $Ab_1$ or $Ab_2$ (anti-idiotypic) reactivity with respect to the sensitizing antigen. Other compositions include specific T cell receptor (TCR) molecules either as T cell clones or hybridomas or as TCR preparations. Immunogenic peptides corresponding to some or all of the complementary determining regions or hyper-variable regions of the TCR are also employed. Such compositions suppress host immune responses to antigen by a variety of pathways including anti-idiotypic interactions with cells involved in antigen processing and stimulation of the immune network. T cell receptor molecules and immunogenic peptides corresponding to regions of the TCR also suppress immune responses by interactions with the immunoregulatory network.

Another embodiment of the invention involves stimulation or introduction of anti-idiotypic antibodies to antibodies reacting with urushiol-MHC complexes. These anti-idiotypic antibodies contain species which react with the combining site on the T cell receptor. These anti-idiotypic antibodies suppress immune responses by blocking TCRs from recognizing antigen-MHC complexes on antigen presenting cells.

The subject compositions represent novel approaches for suppression of immune responses to exogenous antigens and haptens. They are an improvement over prior art compositions employed in suppression of immune responses including desensitization methodologies. They are more effective, rapidly acting and pose reduced risk of host allergic reaction.

The subject compositions generally are effective with some hosts refractory to conventional desensitization or immunosuppressive methodologies. These compositions provide methods for preventing, suppressing or treating disorders resulting from exposure to a variety of exogenous antigens, including allergens.

DETAILED DESCRIPTION OF THE PREFERRED EMBODIMENTS

The present invention provides novel methods and compositions for the modulation or selective suppression of host immune response to an immunogen of interest. Such methods and compositions provide both passive and active introduction and induction of antibodies against antigenic determinants located on immunogens of interest.

The present invention further provides, by way of example, methods for employing antibody compounds in the desensitization of a urushiol sensitive host. Immune responses to the immunogen urushiol are produced by novel methods including immunization with urushiol conjugates to proteins, including MHC preparations. Peptides containing sequences of the common agretope which binds the hapten may also be conjugated to urushiol. In another approach, urushiol is incubated with antigen processing cells such as mouse macrophages or cultured human Langerhans cells and the cell preparations are then used for immunization of a host. Urushiol presented in these forms shows limited or no genetic restriction unlike many other peptide antigens. This makes possible the use of these preparations for vaccination of humans, providing protection against urushiol induced cutaneous sensitivity responses.

In an alternate embodiment, urushiol conjugates such as urushiol-protein and antibodies reacting with urushiol ($Ab_1$) are used as polyclonal antisera or as monoclonal antibodies to induce immunity in human hosts. The monoclonal antibodies may be murine antibodies or chimeric (humanized) antibodies or human antibodies formed by fusion of lymphocytes from a human subject with the human-mouse heteromyeloma EL41.

An antibody, as employed according to the subject invention, is a protein molecule which is generally produced as a result of the introduction of an antigen and which has the ability to combine with the antigen that stimulated its production. Examples include, but are not limited to, immunoglobulin molecules produced by B lymphocytes, T cell receptors, active (antigen-binding) portions thereof, or the like.

Of particular interest with respect to the present invention are anti-idiotypic antibodies ($Ab_2$) to idiotype determinants on antibodies reacting with an immunogen of interest, such as antigenic determinants on the exogenous hapten urushiol. Anti-idiotypic $Ab_2$ antibodies are antibodies directed against portions of the combining site of antibodies that directly bind to antigenic determinants.

According to the present invention, $Ab_2$ antibodies may be provided either by active or passive means. Active immunization means the induction of $Ab_2$ production by the host such as, for example, in response to challenge with $Ab_1$, antibodies from a sensitized host. Passive immunization means the introduction of $Ab_2$ antibodies directly into the host by any of a number of routes of administration, including but not limited to, intravenous (IV), intraperitoneal (IP), intramuscular (IM), oral, or the like. These $Ab_2$ antibodies may be derived from a sensitized host but in the preferred embodiment are monoclonal antibodies. These monoclonal antibodies may be of murine origin or may be in a chimeric (humanized) form. Monoclonal antibodies of human origin may also be employed. Techniques for host immunization are well known to those skilled the art.

It is believed that the compositions of the present invention modulate host immune response by a variety of mechanisms. These include interactions within the immunoregulatory network, one component being the stimulation of T lymphocytes (suppressor T cells) which modulate immune responses. Modulation of antigen processing by antigen presenting cells (APC) such as Langerhans cells and inhibition of recognition of processed antigen-MHC complexes by T cell receptors also may be influenced.

According to the present invention, therapeutic compositions for either active or passive immunization may comprise monoclonal antibody compounds. Techniques for monoclonal antibody production are well known to those skilled in the art. Hybridoma formation and monoclonal antibody production may be achieved by a variety of different techniques which are well known in the art. (See e.g., Goding, J. W., Monoclonal Antibodies: Principles and Practice, Second Ed., Academic Press (1986), which is incorporated herein by reference.)

Those skilled in the art recognize that interactions between processed immunogen-MHC complex and specific TCR molecules is critical in producing an immune response. The present invention provides means for blocking interactions with specific TCR molecules in order to suppress immune responses to exogenous antigens and allergens as exemplified by urushiol-induced contact sensitivity. Active immunization with TCR preparations so as to produce antibodies directed towards particular TCR is one approach accomplished with TCR preparations in the form of specific T cells or TCR preparations. The TCR preparations may also consist of peptides representing the specific portion of the TCR. These immunogenic peptides are constructed by methods well known in the art on the basis of peptide sequences deduced from the nucleotide sequence of the TCR of interest.

Antibodies to specific TCR preparations may also be passively transferred to a host to suppress immune responses to immunogens. These may be obtained from polyclonal antisera or produced as monoclonal antibodies. Such antibodies may be murine monoclonal antibodies or chimeric (humanized) antibodies.

In addition TCR preparations, in particular peptides representing specific TCR sequences, are administered in order to block binding of immunogen-MHC complex with TCR expressed T cells, thereby reducing host immune responses.

Therapeutic compositions according to the present invention may include one or more antibodies, may be a mixture of antibody and adjuvant (including a portion of the antibody such as a peptide, Fab, or $F(ab')_2$, or the like, linked to a toxin or immunogen functioning as an adjuvant, e.g. exotoxin A), and include antibody cocktails. They include T cell receptor preparations or synthetic peptides equivalent to specific TCR sequences. Such compositions may be formulated in a variety of ways for use as clinical formulations. Methods and compositions for formulation of clinical compounds are well known to those skilled in the art.

The subject compositions find utility in a variety of host pathologies. Of particular interest are host allergic reactions to contact sensitizers such as urushiol, an alkylcatechol. The subject compositions, however, find utility in a variety of other conditions. These include, but are by no means limited to, allergy to penicillin or bee sting, allergic bronchopulmonary aspergillosis, chronic active hepatitis, chronic persistent hepatitis, mixed essential cryoglobulinemia, rapidly progressive glomerulonephritis, or the like.

The following examples are offered by way of illustration and not limitation.

EXPERIMENTAL

MATERIALS AND METHODS

I. PREPARATION OF URUSHIOL IMMUNOGEN

A variety of methods for the extraction of urushiol from plant material are known to the art. An example of such a technique is disclosed in U.S. Pat. No. 3,819,726, which is hereby incorporated by reference. While the '726 method is preferred, any extraction method resulting in substantially pure urushiol may be employed with equal utility.

A. Conjugation of alkylcatechol to protein through its N acetyl cysteine intermediate to common protein carriers.

The alkylcatechol pentadecylcatechol (PDC) is oxidized to yield a quinone through reaction with silver oxide. The quinone is then reacted with N-acetyl cysteine to yield N-acetyl S (2,3) dihydroxy-4-pentadecylphenylcysteine. This is purified and conjugated to protein such as HSA or KLH.

DIAGRAM

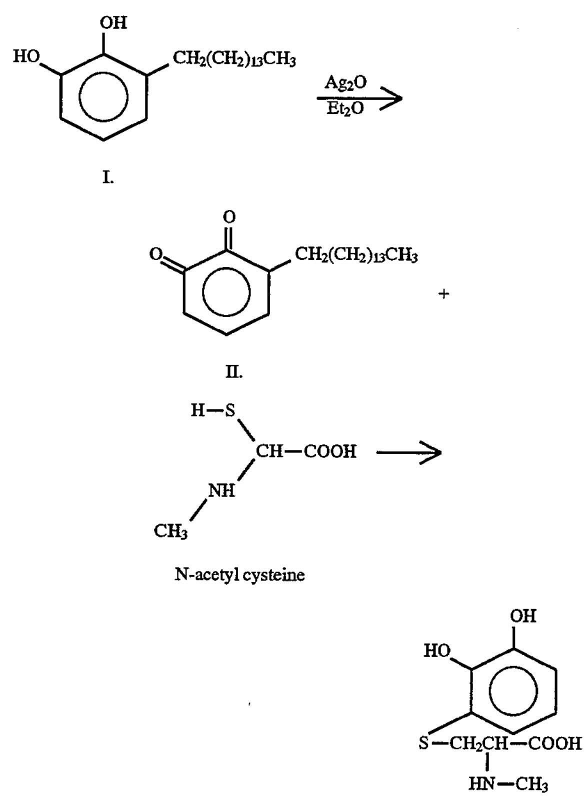

I.

II.

N-acetyl cysteine

III.

B. Reaction with special carriers such as the MHC molecules of humans or animals or portions thereof:

A universal epitope for binding of aromatic rings of azo-linked benzene rings has been postulated (Baskar, S., et al., *Mol. Immunol.* (1990)27:79–86). From this it has been predicted that a cluster of aromatic amino acids (agretope) on the floor of most MHC class II molecule binding sites might provide a strong hydrophobic interaction with aromatic ring-containing haptens, particularly hydrophobic ones such as urushiol. Peptides from lambda repressor protein showed competitive reaction with this agretope. From this known amino acid sequence, sets of amino acids composing proposed patterns in T cell epitopes have been predicted such as amino acids P73–88 and P84–98. These predictions are in agreement with experimental findings (Baskar, supra) showing that these peptides inhibit proliferation of T cell clones by the hapten tyrosine-azobenzenearsonate. Peptides with these sequences (VEEFSPSIAREIYEMY and IYEMYEAVSMQPSLR) are synthesized and conjugated to urushiol by the methods described above, and used as immunogens.

III. GENERAL METHODS OF INDUCTION OF ANTI-URUSHIOL IMMUNOGLOBULIN MOLECULES

Immunoglobulin molecules (Ig) from B lymphocytes to urushiol are induced in mice, rats, rabbits, guinea pigs, or the like by techniques well known to those skilled in the art, wherein such techniques employ urushiol-protein carrier conjugates as previously described. For example, animals are immunized with one or more injections of urushiol-protein conjugates. These are administered by any of several routes including intravenous, subcutaneous, intramuscular and intradermal injection with or without an adjuvant capable of potentiating host immune response. An example of such an adjuvant is complete or incomplete Freund's adjuvant. In some instances, immunoglobulin molecule responses to urushiol are enhanced by deleting immune responses to carrier protein. This is accomplished by elimination of responses to carrier protein by treatment with lymphotoxic drugs using the general procedures described by Thomas, W. A., *J. Immunol. Methods* (1987)97:237–243. Briefly, animals are immunized with carrier protein. At intervals after immunization, animals are treated with cytotoxic drugs, e.g. cyclophosphamide (40 mg/kg body weight) to eliminate lymphocyte clones producing immunoglobulin molecules to carrier protein. Animals are then allowed to recover from this treatment and then immunized with urushiol-protein conjugate. Immunoglobulin molecules are derived from serum of immunized animals. In some cases, mouse and/or rat monoclonal antibodies are produced by hybridoma production with antibody-producing cells e.g. spleen cells from immune donors ($CF_{po3}$).

IV. PRODUCTION OF ANTI-URUSHIOL MONOCLONAL ANTIBODY ($Ab_1$)

A. Murine monoclonal antibodies.

Methods of making murine monoclonal antibodies to an antigen of interest are well known to those skilled in the art and have been described previously. (Goding, supra) For example, spleen cells from urushiol-immune mice are obtained by disaggregation of spleen tissue in serum-free medium (RPMI 1640). Mouse myeloma cells (P3-NS1, Sp 2/0, X63-Ag8.653, NSO/1, or the like) are harvested hen sub-confluent and still in exponential growth and washed in serum free RPMI 1640 medium. Cell preparations are mixed in a ratio of 1 myeloma cell to 5 spleen cells and pelleted by gentle centrifugation in conical-bottomed flasks. The supernatant is removed, cell pellet loosened and polyethylene glycol (PEG 1500) added, 1.8 ml over 2 minutes. The cells are rapidly hand rotated and allowed to stand 2 minutes. Serum free RPMI 1640 medium is added drop-wise (1 ml over 1 minute then 20 ml over 5 minutes) while rotating the tube, then centrifuge. The supernatant is removed and the cell pellet suspended in RPMI 1640 with 15% fetal calf serum and hypoxanthine, methotrexate, and thymidine.

Further growth medium is added and the mixture is plated at $5 \times 10^3$ myeloma cells, 100 μl/well in 96 well flat-bottomed microtiter plates on a feeder layer of rat peritoneal exudate cells. The cells are incubated at 37° C. in 5% $CO_2$. (Galfre, et al., *Nature* (1977)226:550–552). Fusion plates are examined microscopically every 3–4 days and fed by aspirating half of the supernatant from wells and replacing with fresh growth medium. Wells having hybridoma colonies visible to the naked eye are tested for Ig. Murine monoclonal antibodies are obtained from tissue culture supernatants of hybridoma cells grown in vitro. These are purified in various ways, the preferred method being affinity chromatography on a Sepharose-protein A column. In this procedure hybridoma cell supernatants are passed through chromatography columns containing Sepharose-protein A. The bound Ig is then eluted from the column using appropriate media.

B. Production of human monoclonal antibodies.

1. From murine monoclonal antibodies:

The use of murine monoclonal antibodies to produce human monoclonal antibodies by gene fusion techniques are well known to those skilled in the art. They are of two types. The first utilizes the variable region of the murine antibody gene cloned onto a human antibody backbone. The second uses the idiotypic region of the murine monoclonal antibody gene cloned onto a human backbone. (See e.g. Morrison, et al., EPO EP173494 (Mar. 5, 1986); Neuberger, et al., PCT WO-8601533 (Mar. 15, 1986); Robinson, et al., PCT WO-8702671; Morrison, et al., *PNAS, USA* (1984) 81:6851–6855; Boulianne, et al., *Nature* (1984) 312:643–646; Neuberger, al., *Nature* (1985)314:268–270).

Chimeric antibody production involves isolation of messenger RNA (mRNA) from a murine B cell hybridoma producing the relevant monoclonal antibodies. This is then cloned and a complementary DNA library is prepared. See, e.g. Perbal, B., *A Practical Guide to Molecular Cloning*, 2d ed., John Wiley & Sons (1988), which is incorporated herein by reference. The required variable regions of the light and heavy chain genes are then identified with appropriate probes. These are sequenced and made compatible with a constant region gene segment which is also obtained by construction of cDNA preparations and cloning. Heavy and light chain coding sequences are constructed by linkage of the cloned specific immunoglobulin variable (v) gene segment to cloned human constant; gene sequence. On expression in prokaryotic and eukaryotic cells, chimeric antibodies are produced containing the antibody specificity of the mouse monoclonal antibody but with most of the molecule comprising human Ig amino acid sequences.

2. By fusion of human B lymphocytes with a mouse-human heterohybridoma:

Human lymphocytes producing a desired antibody are fused with a mouse-human heterohybridoma cells to produce humanized monoclonal antibodies. The human lymphocytes may be taken from an active urushiol skin lesion or from the peripheral blood.

Mouse/human heteromyeloma EL41 cells (deposited on May 16, 1990 with the European Collection of Animal Cell Cultures and having Accession No. 90051602) as described by Austin, et al., *Immunology* (1989)67:525–530, are fused with human lymphocytes reactive with urushiol using polyethylene glycol according to the method of Galfre, et al., supra. For example, lymphocytes are placed in 30 ml plastic universal bottles and washed twice with growth medium such as Dulbecco's modification of Eagle's medium (DMEM; Flow Laboratories) and the number of lymphocytes is determined by hemocytometer counting. EL41 cells are harvested, washed, and counted in a similar fashion. The two cell populations are then mixed at a lymphocyte:fusion partner ratio of 2:1 and washed for a third time. Following centrifugation the medium is discarded and 0.8 ml of 50% PEG pipetted over a 1 minute period onto the cell pellet with gentle agitation. The mixture is left for 1 minute then 1.0 ml of medium is added over a 1 minute period followed by the addition of 20 ml of medium added slowly over a 5 minute period. The cells are then centrifuged at 1200 rpm for 5 minutes, the medium discarded, and the cells resuspended by gentle pipetting in a 2 ml pipette. Twenty ml of selection medium (DMEM+10% FCS+$10^{-4}$M hypoxanthine +$10^5$M methotrexate +$10^6$M thymidine) is finally added to the cell suspension and the cells aliquot ed into two 96 well tissue culture microtiter plates containing rat peritoneal exudate cells ($2.5 \times 10^3$/well) as a feeder layer. An additional 100 µl of media is also added to each well. The selection medium is changed every 72 hours until resulting hybridomas have reached 50% confluence then every 48 hours. The growth of hybridomas is regularly checked and when the colonies cover 50% of the well the supernatant is analyzed for Ig. Hybridomas producing Ig of interest are immediately cloned. Established hybridomas are frozen down in aliquots of $20 \times 10^6$ cells/ml in 95% FCS and 5% dimethylsulfoxide (DMSO) and stored in liquid nitrogen.

V. PRODUCTION OF ANTI-URUSHIOL T CELL RECEPTORS FOR USE AS IMMUNOGENS

Mice are vaccinated against haptens (oxazolone, DNFB), including urushiol, by immunization with T cells derived from lymph nodes of hapten sensitized donors. Nice are vaccinated by immunization with urushiol specific T cells. These may be cloned T cells, T cell hybridomas, or peptides mimicking the TCR of the specific T cells.

A. Production of urushiol specific T cell lines from sensitized mice.

BALB/c mice are sensitized following application of urushiol (0.01–5 mg) in acetone onto the dorsal skin. T cells from sensitized mice are obtained from several sources including lymph nodes or urushiol-induced cutaneous lesions and expanded in culture by in vitro stimulation with urushiol or urushiol-polymer conjugates using stimulation procedures well known to those skilled in the art. Urushiol specific T cell clones or T cell hybridomas are obtained by fusion of T cells with murine thymoma cells (BW 5147 cells as described by Bigby, M., et al., *J. Immunol.* (1989) 143:3867–3872). These cells produce immune responses to urushiol specific TCR. Such cells have utility as T cell vaccines which may be one of several types including viable or attenuated T cells and T cells modified by cross linking with agents such as glutaraldehyde (Cohen, I. R., and Weiner, H. L., *Immunol. Today* (1988)9:332–335). The TCR of the urushiol responding-T cell clone is identified by reaction with monoclonal antibodies which detect variable segments of the TCR (Kappler et al., *Nature* (1988) 332:35–40).

In another approach, messenger RNA or DNA from cloned T cells reacting with urushiol are probed either directly or after amplification by polymerase chain reaction by specific hybridization with nucleic acid probes for TCR gene families using hybridization methods well known to those skilled in the art. The TCR sequence (in part) is obtained from the amplified DNA or RNA. Regions of TCR amino acid sequences are selected on the basis of their immunogenic or antigenic properties identified using algorithms to predict T cell helper/cytotoxic determinants (Rothbard, J. B., and Taylor, W. R., EMBO (1988) 7:93–100). For example, peptides containing 14 or 15 amino acids are predicted to contain specific TCR sites for urushiol. Peptides of selected amino acid composition are then synthesized using standard procedures well known to those skilled in the art. Synthetic peptides are then used to vaccinate animals.

B. TCR produced from immune human donors.

T lymphocyte clones are established from peripheral blood mononuclear cells (PBMC) or contact dermatitis lesions derived from urushiol sensitized human subjects by methods generally described by Kalish and others. (Kalish, R. S., and Morimoto, C., *J. Clin. Invest.* (1988)82:825–832; *J. Invest. Dermatol.* (1989)92:46–52). PBMC isolated from venous blood by Ficoll-Hypaque separation are cultured in IL-2 containing media and sensitized or expanded by inducing proliferation in vitro by the addition of urushiol in dimethylsulfoxide or on autologous PBMC (Byers, V., et al., *J. Clin. Invest.* (1979)64:1437–1448). Other growth factors such as IL-4 may be used (Paliard, et al., *J. Immunol.* (1989)81438,452–457). Following culture for a period of time to establish satisfactory cell growth, cells are cloned by limiting dilution using standard cell culture techniques. Cells are then grown and positive wells expanded. This phase may include further stimulation of cells with urushiol and autologous irradiated (5000R) PBMC as feeder cells. T cell clones are then established by standard techniques. Alternatively, T cell hybridomas may be employed as a source of TCRs. The T cell vaccine may be composed of one or more formulations including viable or attenuated T cells and T cells modified by cross linking agents, e.g. glutaraldehyde (Cohen, supra). Ideally, T cell vaccines should be of autologous origin since responses are generally restricted by the MHC component of the TCR (Schwartz, R., *Ann. Rev. Immunol.* (1985)3:237–261). Since broad MHC restriction is, however, involved in the recognition of certain haptens and antigens (Panina-Bordrgnon, et al., *Eur. J. Immunol.* (1989)19:2237–2242). [An alternative approach is to administer vaccines composed of pooled preparations of cloned T cells derived from a number of allogeneic donors.]

In another approach, specific antigen binding regions of the TCR may be identified, and the peptide comprising that region synthesized as described previously for use as an immunogen.

VI. PRODUCTION OF MONOCLONAL ANTI-IDIOTYPIC ANTIBODIES ($Ab_2$)

A. Murine monoclonal antibodies.

BALB/c mice are immunized with purified mouse monoclonal antibodies reacting with alkylcatechols such as urushiol as previously described. These antibodies are injected in various forms including antibody emulsified in Freund's complete adjuvant (CFA) and antibody-key hole limpet hemocyanin conjugates with or without CFA. Immunization is carried out at intervals of 2–3 weeks until the serum contains appropriate levels of anti-idiotypic Ig as detected by the method described below. Hybridomas are then produced by fusion of spleen cells from immune mouse with mouse myeloma cells. The detailed procedure has been previously described above. Murine monoclonal anti-idiotypic antibodies are obtained from tissue culture supernatants of hybridomas. These are purified in various ways such as by affinity chromatography on Sepharose-protein A or on immobilized anti-urushiol monoclonal antibody.

B. Production of human anti-idiotypic monoclonal antibodies.

Lymphocytes taken from the urushiol lesions or peripheral blood of humans undergoing oral desensitization to urushiol are fused with the murine-human heterohybridoma EL41 as described above. The clones are then screened to identify those reacting with anti-urushiol antibodies, human or murine, using screening procedures described below. Alternatively, murine monoclonal antibodies may be chimerized by gene cloning procedures or humanized as described above.

VII. PRODUCTION OF ANTIBODIES AGAINST URUSHIOL TCR

In another approach, antibodies are produced against urushiol TCRs, in the expectation that these antibodies would have a specificity complementary to the TCR which recognizes urushiol in combination with a portion of the MHC. T cell lines are produced from lymphoid cells derived from urushiol sensitized BALB/c mice. These are generated either as T cell clones using known techniques (Baskar, S., et al., supra) or by the construction of T cell hybridomas (Baskar S., et al., Euro. J. Immunol (1990)20:587). Urushiol sensitized T cell lines are selected by their capacity to respond to urushiol. This can be demonstrated by showing that the T cell lines undergo proliferative responses to urushiol. Urushiol sensitized T cell lines are used to induce anti-TCR monoclonal antibodies by immunization of mice. (Owhashi, M. and Heber-Katz, E, *J. Ex. Med.* (1988) 168:2153). Antibodies are assayed using techniques such as flow cytometry to demonstrate antibody binding to T cell clones or hybridomas. The antibodies are also shown to inhibit urushiol induced proliferation of T cell lines. Finally anti-TCR monoclonal antibodies are selected by showing that they suppress the induction of DTH to urushiol in murine model systems. Selected anti-TCR antibodies may be used clinically as murine antibodies or humanized and employed clinically.

VIII. DETECTION OF ANTI-IDIOTYPIC ANTIBODY

Anti-idiotypic monoclonal antibodies to murine monoclonal antibodies reacting with urushiol are detected by blocking assays. Monoclonal anti-urushiol antibody binds to urushiol-containing antigen preparations eg. urushiol human serum albumin, described previously. This can be detected in several ways, the preferred method being an ELISA test. Such tests are well known to those skilled in the art. In this test mouse monoclonal antibody bound to urushiol conjugate is detected by a second reaction with enzyme-linked anti-mouse immunoglobulin antibody. To detect anti-idiotypic antibody the preparation is mixed with the monoclonal antibody, and the interaction of the anti-idiotypic monoclonal antibody is then detected by the reduction of reaction of the mouse anti-urushiol antibody with urushiol in the ELISA test.

EXPERIMENTAL STUDIES

EXAMPLE I

Suppression of the Immune Response to Urushiol with Polyclonal Sera from Sensitized Mice Sera from BALB/c mice taken 20–28 days after sensitization and challenge with urushiol are transferred to naive mice and these are then challenged with urushiol. (Dunn, et al., *J. Invest. Derm.* (1987)89:296–298). Sensitization to urushiol is obtained by painting the compound (dose 0.1 to 5 mg) in acetone (100 μl) onto the abdomen. Sensitization to urushiol is determined 4 to 5 days later by application of urushiol (5 to 50 μg) in acetone (10 μl) to one ear. The other ear is treated with acetone alone. Ear thickness is measured with a micrometer at 48 and 72 hours after challenge and the difference between urushiol-challenged and control ears measured. Mean values of ear thickness increments are obtained for each group of 6–8 mice and compared by Student's T test. Control mice include those treated with acetone solvent and urushiol sensitized mice ear tested with an unrelated hapten, e.g. dinitrochlorobenzene. The response to anti-urushiol antibody treatment is indicated by a significant decrease in ear swelling following skin sensitization with urushiol and/or an increase in the dose of urushiol required to produce ear swelling.

EXAMPLE II

Suppression of Immune Responses to Urushiol In Mice Using Polyclonal Sera from Hyposensitized Humans The IgG fraction of sera taken from human donors hypersensitive to urushiol, and hyposensitized by oral administration of urushiol over a period of 6–8 months was given to BALB/c mice 8 days before attempted sensitization with urushiol (sensitization and challenge protocol as in Example (Epstein, W., et al., supra). The IgG fractions were purified by affinity chromatography, resuspended in an amount equivalent to the initial serum volume, and administered intravenously in a volume of 0.5 ml/mouse. The sensitization to urushiol, as measured by ear swelling after challenge was significantly decreased in mice receiving such injections, and was antigen specific.

EXAMPLE III

Suppression of Immune Response to Urushiol: Treatment with Monoclonal Anti-Urushiol Antibody Murine anti-urushiol monoclonal antibodies are administered to BALB/c mice either before or following skin sensitization with urushiol. Various time schedules for antibody administration are used, such as three daily injections before urushiol treatment, or antibody administration up to 48 hours following urushiol. Doses of anti-urushiol antibody are administered in a range of 25 μg to 1 mg/dose. Sensitization to urushiol, and challenge is carried out as described above in Example I.

EXAMPLE IV

Suppression of Immune Responses to Urushiol In Mice by Treatment with T Cell Receptor (TCR) from Urushiol Sensitized Lymphocytes TCR immunization with T cells derived from sensitized animals, cloned lines of T cells, or T cell hybridomas are given before exposure to urushiol. A similar approach is employed with peptides containing the immunogenic region of the TCR. Additionally, TCR preparations may be isolated from sensitized cells by a number of procedures such as immunoprecipitation with anti-TCR antibodies including monoclonal antibodies. Peptides containing the immunogenic regions of urushiol specific TCR may also be used alone or following conjugation of carrier proteins such as keyhole limpet hemocyanin to render them more immunogenic. They may be given by several routes including subcutaneous and intravenous injection and immunological adjuvants such as alum or Freund's adjuvant may be used.

These vaccines may be given 1–15 days prior to attempted sensitization, or to mice previously sensitized to urushiol. In both cases the sensitization and challenge protocol is as described earlier in Example I. The system in which sensitized animals are given the vaccine is used to confirm that treatment will suppress cutaneous sensitivity responses as a model for human poison ivy/oak dermatitis.

EXAMPLE V

Suppression of Immune Response to Urushiol: Treatment with Monoclonal Anti-Idiotypic Antibody.

Murine ant-i-idiotypic antibody reacting with monoclonal antibody directed against, urushiol either alone or coupled to a common carrier, or coupled to a portion of an MHC molecule, or against the urushiol TCR are administered to BALB/c mice either before or after skin sensitization with urushiol. Various time schedules of anti-idiotypic antibody administration are used such as three daily injections before urushiol sensitization or treatment at intervals after urushiol. Doses of anti-idiotypic antibody range up to 1 mg/dose. Murine anti-urushiol monoclonal antibodies are administered to BALB/c mice either before or following skin sensitization with urushiol. Sensitization and challenge to urushiol is performed as described above in Example I. The response to anti-idiotypic antibody treatment is indicated by a significant decrease in ear swelling following treatment with urushiol and/or an increase in urushiol dose requirements to produce sensitization.

EXAMPLE VI

Suppression of Immune Response to Urushiol by Treatment of Human Subjects with Monoclonal Anti-Urushiol Antibody Anti-urushiol antibody is administered to suppress delayed type hypersensitivity (DTH) responses to poison ivy/oak. The monoclonal antibodies may be murine monoclonal antibodies or chimerized products, as described previously, constructed by inserting mouse antibody variable regions into human constant heavy and light chains. Chimeric antibody technology is well known to those skilled in the art. (Morrison, et al., supra). Another approach, complementary determining region grafting (CDR), involves incorporation of CDRs of anti-urushiol murine monoclonal antibody into an expression system encoding human variable and constant regions (Jones, et al., supra). The anti-urushiol monoclonal antibodies may be murine antibodies, human antibodies produced by in vitro growth of human antibody producing cells, or humanized murine antibodies. These are obtained in several ways including fusion of antibody producing lymphocytes with human/mouse heteromyeloma cells (Austin, et al., supra).

Anti-urushiol antibody preparations are administered by one or more routes such as intravenously or intramuscularly. They may be administered to prevent sensitization to urushiol or in subjects already sensitized to decrease reactivity. The human injections may range from 1 to 10 given over periods of time up to a month and repeated treatments may be given at 6–12 month intervals.

EXAMPLE VII

Suppression of Immune Response to Urushiol by Treatment of Human Subjects with Monoclonal Anti-Idiotypic Antibodies Anti-idiotypic antibodies binding the urushiol reactive monoclonal antibody or the urushiol TCR are administered to prevent sensitization or to suppress delayed type hypersensitivity (DTH) responses in subjects exposed to poison ivy/oak. The monoclonal antibodies may be murine monoclonal antibodies or chimerized products, as described previously, constructed by inserting mouse antibody variable regions into human constant heavy and light chains. Chimeric antibody technology is well known to those skilled in the art. (Morrison, et al., supra). Another approach, complementary determining region grafting (CDR), involves incorporation of CDRs of anti-idiotypic murine monoclonal antibody into an expression system encoding human variable and constant regions (Jones, et al. supra).

The anti-idiotypic monoclonal antibodies may be murine antibodies, human antibodies produced by in vitro growth of human antibody producing cells, or humanized murine antibodies. These are obtained in several ways including fusion of antibody producing lymphocytes with human/mouse heteromyeloma cells (Austin, et al., supra).

Anti-idiotypic antibodies are administered by one or more routes such as intravenously, intradermally, orally, or the like. To prevent sensitization, antibody is administered before exposure (or re-exposure) to poison oak/ivy. To suppress DTH responses antibody is administered to sensitized individuals before exposure.

EXAMPLE VIII

Suppression of Immune Response to Urushiol in Humans by Immunization with T Cell Receptor Clones of urushiol sensitized T lymphocytes from sensitized individuals are produced by continual antigen challenge in vitro in the presence of IL-2, and the gene of the TCR is cloned. This is then used for vaccination of animals or humans before exposure to urushiol.

These TCRs or synthetic peptides mimicking portions of their reactive site are given before exposure to urushiol in BALB/c mice to prevent sensitization. For example, normal mice are immunized with the peptide vaccine either alone or coupled to a protein carrier such as key hole limpet hemocyanin and adjuvants such as Freund's complete adjuvant or Quil A are used. Treated mice are then exposed to urushiol (0.1 to 5 mg) by skin application acetone and the effect of peptide treatment is determined by ear challenge with urushiol.

Peptide immunization may also be given to mice sensitized to urushiol to prevent or suppress responses. In this case mice that were previously exposed to urushiol are immunized by peptide formulations as outlined above, and challenged by exposure to urushiol by ear painting and the effect of treatment is assessed by reduction in the size of the ear swelling.

It will be apparent to those of skill in the art that the present invention adds to the state of the art novel compositions and methods useful in the modulation of host immune response to an immunogen. The subject antibody compositions are an improvement over prior desensitization methodologies in that the risk of host allergic reaction to the compositions is very low.

Although the present invention has been described in some detail for the purposes of clarity and understanding, it will be obvious to those skilled in the art that certain changes and modifications may be practiced within the scope of the appended claims.

What is claimed is:

1. A method for selective suppression of an immune response to urushiol, comprising vaccinating a human with an effective amount of a monoclonal antibody to urushiol to suppress a T cell mediated immune response to urushiol in said human.

2. A method for treating a human having urushiol-induced contact dermatitis, comprising vaccinating a human having urushiol-induced contact dermatitis with an effective amount of a monoclonal antibody to urushiol to alleviate said dermatitis.

3. A method for selective suppression of urushiol-induced contact dermatitis, comprising vaccinating a human with an effective amount of a monoclonal antibody to urushiol to suppress urushiol-induced contact dermatitis in said human.

4. A method for selective modulation of urushiol-induced contact dermatitis, comprising vaccinating a human with an effective amount of a monoclonal antibody to urushiol to modulate urushiol-induced contact dermatitis in said human.

5. A method for selective modulation of an immune response to urushiol, comprising vaccinating a human an effective amount of a monoclonal antibody to urushiol to modulate a T cell mediated immune response to urushiol in said human.

6. The method of claim 1, 2, 3, 4 or 5, wherein the monoclonal antibody is administered together with a pharmaceutically acceptable adjuvant.

7. A monoclonal antibody to urushiol.

8. A composition comprising a monoclonal antibody to urushiol and a pharmaceutically acceptable adjuvant.

* * * * *